United States Patent [19]

Wang et al.

[11] Patent Number: 4,705,820

[45] Date of Patent: Nov. 10, 1987

[54] SURGICAL SUTURE COATING

[75] Inventors: David W. Wang, Vestal, N.Y.; Donald J. Casey, Ridgefield; Leonard T. Lehmann, Danbury, both of Conn.

[73] Assignee: American Cyanamid Company, Stamford, Conn.

[21] Appl. No.: 903,791

[22] Filed: Sep. 5, 1986

[51] Int. Cl.$^4$ .............................................. C08L 67/04
[52] U.S. Cl. .................................... 524/381; 523/105; 523/113; 528/354; 528/361; 427/2
[58] Field of Search .................... 528/354, 361; 427/2; 523/113, 105; 524/381

[56] References Cited

U.S. PATENT DOCUMENTS

| | | | |
|---|---|---|---|
| 3,867,190 | 2/1975 | Schmitt et al. | 427/2 |
| 3,982,543 | 9/1976 | Schmitt et al. | 427/2 X |
| 4,243,775 | 1/1981 | Rosensaft et al. | 528/354 X |
| 4,300,565 | 11/1981 | Rosensaft et al. | 528/354 X |
| 4,429,080 | 1/1984 | Casey et al. | 528/354 X |
| 4,496,446 | 1/1985 | Ritter et al. | 523/113 X |

*Primary Examiner*—Earl Nielsen
*Attorney, Agent, or Firm*—David A. Warmbold; Charles F. Costello, Jr.

[57] ABSTRACT

A surgical suture coating comprising a random copolymer is disclosed. The copolymer has about 25 to 75 weight percent of glycolic acid ester linkages. The remaining linkages comprise at least trimethylene carbonate. The copolymer has a glass transition temperature at or below ambient temperature.

11 Claims, No Drawings

SURGICAL SUTURE COATING

BACKGROUND OF THE INVENTION

This invention relates to a random copolymer prepared from cyclic monomers of glycolide and trimethylenecarbonate. The random copolymer may also include other cyclic monomers such as lactide, caprolactone, and p-dioxanone.

This invention also relates to compositions useful as a coating and lubricating finish for surgical devices, preferably for multifilament bioabsorbable sutures.

A block copolymer of glycolide and trimethylenecarbonate is known in the preparation of a synthetic absorbable suture, e.g. as disclosed in U.S. Pat. Nos. 4,243,775 and 4,300,565. These patents are incorporated herein by reference. The block copolymer disclosed in the prior art is highly crystalline, high melting (more than about 200° C.), and is a fiber forming material. The block copolymer exhibits good physical properties and good absorption times when implanted in living animals.

It is known that suture materials are often coated with various substances to improve their handling characteristics, for example U.S. Pat. No. 4,027,676 and 4,185,637 teach the use of a composition comprising a bioabsorbable polymer and a fatty acid salt for suture coating application, and U.S. Pat. No. 4,047,533 describes the use of water soluble poly(alkylene oxide)s as a coating for multifilament bioabsorbable sutures. However, there is a constant research effort in this field to improve suture handling characteristics. For example, a survey included in U.S. Pat. No. 4,047,533 outlines several other approaches which are useful in improving the knot tying performance of sutures. All of the above patents are incorporated herein by reference.

It is an object of this invention to provide a random copolymer of glycolide and trimethylene carbonate containing up to about seventy-five weight percent of glycolide. The random copolymer can be processed by a solution method or by melting it at a moderate temperature to form a film and various articles.

Another object of this invention is to provide bioabsorbable, water insoluble coatings for multifilament sutures or implantable devices. The preferred coating systems may be applied to any suture material where it is desired to improve fiber lubricity and suture knot rundown characteristics. The coating is particularly useful with synthetic absorbable multifilament sutures composed of polylactide, polyglycolide, copolymers of lactide and glycolide, copolymers of glycolide and trimethylene carbonate, poly(p-dioxanone), poly(alkylene oxalate), and copolymers of glycolide and alkylene oxides, etc.

SUMMARY OF THE INVENTION

A suture coating comprising a random copolymer has been invented. The copolymer has about 25 to 75 weight percent of glycolic acid ester linkages. The remaining linkages comprise at least trimethylene carbonate. The copolymer has a glass transition temperature at or below ambient temperature.

In one embodiment, the glycolic acid ester linkages comprise from about 45 to 65 percent. In a specific embodiment, the glycolic acid ester linkages are about 50 percent. In another embodiment, the inherent viscosity of the coating as measured on a 0.5% solution is hexafluoroacetone sesquihydrate is between 0.5 and 3 dl/g.

A suture coating for a bioabsorbable suture has also been invented. The coating comprises a bioabsorbable random copolymer having up to abot 75 weight percent of glycolic acid ester linkages. The remaining linkages comprise at least trimethylene carbonate. The copolymer has a glass transition temperature at or below ambient temperature.

In one embodiment, the glycolic acid ester and trimethylene carbonate linkages are each about 50 percent. In another embodiment, the inherent viscosity of the coating is from 0.5 to 3 dl/g. In yet another embodiment, the in vivo absorption time of the coating is less than one year.

A suture coating for a synthetic bioabsorbable suture has been invented. The coating comprises a bioabsorbable random copolymer having up to about 75 weight percent of glycolic acid ester linkages. The remaining linkages comprise trimethylene carbonate. The copolymer has an in vivo absorption time in living animal tissue of less than one year, an inherent viscosity of 0.5 to 3.0 dl/g, and a glass transition temperature of less than about 25° C. In combination with the copolymer is a lubricant additive of a stearoyl lactylate having the formula:

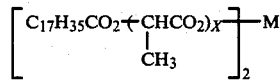

wherein X is at least two and M is an alkaline-earth metal.

In one embodiment, the glycolic acid ester linkages are about 50 percen. In another embodiment, the glass transition temperaure of the copolymer is 0° to 5° C.

The coatings allow easier knot tying and reduce tissue drag for multifilament sutures. Because the coatings are insoluble in water, they will not be washed off by the first pass of the suture through tissue and thus will retain their lubricant performance while wet.

A random copolymer of glycolide and trimethylene carbonate containing less than sixty weight percent of glycolide has good solubility in organic solvents such as chloroform and methylene chloride. It is particularly suitable for use as a bioabsorbable coating material, for example as a coating for a surgical suture or other wound closure element. Specifically, a multifilament synthetic absorbable suture coated with a bioabsorbable random polymer of this invention exhibits known "rundown" performance that is superior and unexpected from similar uncoated samples.

Several properties of the random copolymers of this invention make them particularly useful as a lubricant coating for an absorbable surgical device. The following is a summary of the most pertinent properties:

Coating Material a. The random copolymer contains glycolide units and will therefore readily adhere to a glycolide-containing absorbable braided suture.

b. The random copolymer contains enough glycolide units to be readily bioabsorbed.

c. The random copolymer contains enough comonomer units to be readily soluble in common organic solvents. This solubility permits convenient coating from a solution of the copolymer.

d. The random copolymer is not soluble in body fluids. Therefore, the random copolymer does not wash off on the first pass of a suture through living tissue. The random copolymer can also retain its lubricant properties while wet.

e. The random copolymer is amorphous, has a low glass temperature, and has a high enough molecular weight to have relatively good tensile strength. These characteristics prevent the copolymer from being brittle and easily flaked off the suture.

f. The absorption characteristics make the random gly/TMC coating compatible with the absorption profiles of sutures manufactured from the polymer prepared almost entirely from glycolide, or from copolymers prepared from glycolide and lactide or glycolide amd TMC or other glycolide containing copolymers.

DESCRIPTION OF THE INVENTION

A random copolymer of glycolide and trimethylene carbonate containing less than sixty weight percent of glycolide has good solubility in many organic solvents. The random copolymer is particularly useful as a bioabsorbable coating material for a surgical suture and for surgical devices. A multifilament synthetic absorbable suture coated with the bioabsorbable polymer of this invention exhibits knot run-down performance that is superior and unexpected.

The random copolymer of this invention is amorphous and has a relatively low glass transition temperature. The random copolymer also has a relatively high molecular weight. The relatively high molecular weight enables the random copolymer to have reasonable tensile strength. The combined chemical and physical properties prevent the copolymer from being brittle and easily flaking off the surface of a suture. Finally, the copolymer contains enough glycolide units to be bioabsorbable.

The random copolymer contains enough nonglycolide comonomer units to be readily soluble in common organic solvents. This solubility permits convenient coating from a solution of the polymer. Also, the copolymer contains enough glycolide units so it readily adheres to a glycolide-containing absorbable braided suture.

The random polymer can be plasticized by various agents such as glyceryl triacetate, butyl citrate, ethyl benzoate, dibutyl phthalate, etc. Various additives can also be included in the formulation to improve the performance. Further, known lubricants can be included such as calcium stearate or other salts of fatty acids, calcium stearoyl lactylate, sodium stearoyl lactylate, a bioabsorbable polyester-carbonate salt, or a bioabsorbable polyester salt such as:

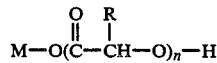  (I)

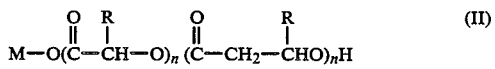  (II)

wherein M is an alkali metal, for example sodium, an alkaline earth, for example calcium or magnesium, or hydrogen, or a combination of these. The bioabsorbable polyester salts of formulas (I) and (II) are discloed respectively in U.S. Pat. No. 4,010,196 with the proviso, as taught by this patent, that M is not calcium, and Great Britain Pat. No. 1,207,588. These patents are incorporated herein by reference. Finally, a water soluble lubricant such as poly(alkylene oxide) can be added.

The random copolymer of this invention is not soluble in body fluids. The copolymer, therefore, will not be washed off by the first pass of a coated suture through tissue. Also, the copolymer can retain its lubricant properties while wet.

Poly(glycolide-co-trimethylene carbonate)s are bioabsorbable materials. They offer good biocompatibility and are specially useful as coatings or coating binders for bioabsorbable multifilament sutures. When used as coating materials, glycolide-trimethylene carbonate random copolymers improve the knot run-down performance of multifilament sutures. The polymers can also be used as binders to hold lubricants in place on the surface of a suture in order to resist the displacement of the lubricant by friction during the knotting process.

A 50% glycolide/50% TMC copolymer is a good coating material. This ratio makes the glycolide/TMC coating compatible with the absorption profile of a Dexon® (American Cyanamid Co., Wayne, N.J.) homopolyglycolic acid suture.

The random copolymer of this invention can be prepared by the ring opening copolymerization of glycolide and trimethylene carbonate in the presenceof a suitable catalyst, such as $SnCl_2.2H_2O$, stannous octoate, zinc powder and the like. The polymerization is initiated by compounds containing one or more hydroxyl groups. The reaction is conducted with very pure and dry reactants, and under an inert gas atmosphere. The temperature of the reaction is sufficient to maintain the reaction mixture in a molten state until the polymerization is completed.

The random copolymer obtained is characterized by having an inherent viscosity 0.5 to 3.0 dl/g as determined on a 0.5% solution of the polymer in hexafluoroacetone sesquihydrate at 30° C.

A 50% glycolide/50% trimethylene carbonate random copolymer has been evaluated as a coating material for a braided surgical suture containing essentially one hundred percent of glycolic acid ester linkages.

The random copolymer and the method of preparing the copolymer of this invention are described in the following examples.

EXAMPLE 1

Glycolide (5.5 g), trimethylene carbonate (4.5 g), 1.45 ml of a solution of $SnCl_2.2H_2O$ in diethyl ether (conc. 0.429 mg/ml), and 0.216 of a solution of diethylene glycol in diethyl ether (conc. 1% v/v) were placed in a single neck 25 ml round-bottomed flask. After the diethyl ether was removed under reduced pressure, the flask was sealed with a stopcock and immersed in an oil bath heated at 180° C. The temperature of the oil bath was raised to 210° C. in 55 minutes. Heating was continued at 210° C. for another 145 minutes. The cooled polymerization product was removed from the flask and was dried under vacuum at 80° C. overnight.

The copolymer has a glass transition temperature (Tg) of 9° C. and was amorphous by DSC determination. The inherent viscosity was 1.24 dl/g. As determined by NMR, the product was a 59/41 (by weight) copolymer of glycolide and trimethylene carbonate. The residual trimethylene carbonate monomer level was around 2 weight percent.

EXAMPLE 2

Into a heated polymerization reactor was charged 45 g of glycolide, 55 g of trimethylene carbonate (TMC), 9.23 mg of $SnCl_2.2H_2O$, and 97.2 μl of diethylene glycol (hereafter abbreviated as DEG). The reaction mixture was heated with stirring under dry nitrogen at 186° C. for 75 min.

The resulting copolymer was discharged as a viscous melt which was cooled and ground to fine particles. The ground copolymer was dried under vacuum at 60° C. overnight. The copolymer had a composition of 47.7 weight percent trimethylene carbonate and 52.3 weight percent of glycolide. Less than 2.5 percent of monomeric trimethylene carbonate was also present. The inherent viscosity was 0.98 dl/g.

EXAMPLE 3

Glycolide (4.5 g), trimethylene carbonate (5.5 g), 1.62 ml of a solution of $SnCl_2.2H_2O$ in diethyl ether (conc. 0.429 mg/ml), and 0.243 ml of a solution of diethylene glycol in diethyl ether (conc. 1% v/v) were placed in a single neck 25 ml round bottom flask. After the diethyl ether was removed under reduced pressure, the flask was sealed with a stopcock and immersed in an oil bath at 180° C. After 2 hours, the temperature was raised to 210° C. and heating was continued for an additional 1 hour. The cooled polymer was removed from the flask, ground in a mill, and dried under reduced pressure at 80° C. overnight. The final copolymer was a 47.4/52.6 (by weight) copolymer of glycolide and trimethylene carbonate. The Tg was 2° C. and the inherent viscosity was 1.46 dl/g.

EXAMPLE 4

To a 25 ml round-bottomed flask was charged 3.5 g of glycolide, 6.5 g of TMC, 1.62 ml of a solution of $SnCl_2.2H_2O$ in diethyl ether (conc. 0.429 mg/ml), and 0.243 ml of a solution of diethylene glycol in diethyl ether (conc. 1% v/v). After the diethyl ether was removed under reduced pressure, the flask was sealed with a stopcock and heated at 165° C. for one hour. Heating was then continued at 180° C. for an additional 3 hours. The product was cooled, ground, and dried at 75° C. under vacuum overnight. The copolymer was a 35/65 weight percent copolymer of glycolide and trimethylene carbonate. The residual trimethylene carbonate level was around 3 weight percent. The inherent viscosity was 1.65 dl/g and the glass transition temperature was −5.5° C. as determined by DSC.

EXAMPLE 5

A 65.6/34.4 weight percent copolymer of glycolide and trimethylene carbonate was synthesized according to the procedure outlined in Example 2 except that the reaction temperature was 180° C. The ingredients and their quantity charged to the reactor were as follows:

| | |
|---|---|
| Glycolide | 72 g |
| TMC | 48 g |
| $SnCl_2.2H_2O$ | 7.4 mg |
| DEG | 0.0518 ml |

The inherent viscosity of this material was 0.99 dl/g.

EXAMPLE 6

A 71.3/28.7 weight percent copolymer of glycolide and trimethylene carbonate was synthesized according to the procedure outlined in Example 2 except that the reaction temperature was 185° C. The ingredients and their quantity charged to the reactor were as follows:

| | |
|---|---|
| Glycolide | 80.4 g |
| TMC | 39.6 g |
| $SnCl_2.2H_2O$ | 7.3 mg |
| DEG | 0.0256 ml |

The inherent viscosity of this product was 0.91 dl/g.

EXAMPLE 7

A 74.3/25.7 weight percent copolymer of glycolide and trimethylene carbonate was prepared according to the procedure outlined in Example 4 except that the reaction temperature was 180° C. for 55 minutes, and then was raised to 210° C. for 2 hours and 25 minutes. The ingredients and their quantity charged to the reactor were as follows:

| | |
|---|---|
| Glycolide | 98.5 g |
| TMC | 36.45 g |
| $SnCl_2.2H_2O$ | 8.17 mg |
| DEG in ether (1% v/v) | 2.86 ml |

The inherent viscosity of the copolymer was 1.07 dl/g.

EXAMPLE 8

To a round-bottomed flask was charged 7.5 g of L-lactide, 2.5 g of trimethylene carbonate, 3.62 ml of a solution of $SnCl_2.2H_2O$ in diethyl ether (conc. 0.429 mg/ml) and 0.181 ml of a solution of diethylene glycol in diethyl ether (conc. 1% v/v). The polymerization was carried out according to the procedure outlined in Example 1. The product was an amorphous 74.6/25.4 copolymer of L-lactide and trimethylene carbonate with an inherent viscosity of 0.81 dl/g and a glass transition temperature of 31° C.

The preferred coating polymr is approximately 50/50 (wt %) glycolide/trimethylene carbonate copolymer. Tests indicate that this copolymer and mixtures of the polymer with calcium salts such as calcium stearate or calcium stearoyl lactylate are promising coating materials for DEXON® braid. They perform well under both dry and wet conditions.

The method and the product of the present invention are further illustrated by the following examples.

A 52.3/47.7 random glycolide/TMC copolymer of Example 2 was formulated as follows for evaluation as a coating for braided absorbable sutures.

Coating Formulation 1

6.0 grams of copolymer
9.0 grams of Xylene
80.0 grams of Methylene Chloride

Coating Formulation 2

6.0 grams of Calcium Stearoyl Lactylate (Verv TM)*
1.6 grams of copolymer
9.0 grams of Xylene
80.0 grams of Methylene Chloride

*C. J. Patterson Co., Kansis City, MO, U.S.A.

Coating Formulation 3

3.0 grams of Calcium Stearoyl Lactylate (Verv)
3.0 grams of copolymer 4.5 grams of Xylene 40.2 grams of Methylene Chloride A 20' length of size 2/0 polyglycolic acid braid was formed into a skein and immersed in each of these solutions for 5 minutes. The skeins were then removed, allowed to drain, and were dried for 1 hour. The dried strands were then separated and cut into suitable lengths.

Each length was then tied around a conventional tubular rubber tying board as follows:

A single throw was made and then run down to the tubing to assess the resistance of the knot to rebound (the ability of the single throw to remain in position after the run-down is complete). A square knot was then formed and run down to the tubing to assess the stick-slipping of the knot (chatter) as it runs down and to assess the force required to initiate and sustain the run-down.

The rating system used to evaluate these coatings was:

Excellent (a) No stick-slip during run down. (b) Moderate force required which does not result in damage to the sleeve fibers of the suture. (c) No rebound of the single throw.

Good (a) No stick-slip during run down. (b) Run-down force is a little high, but no damage is done to the sleeve fiber. (c) Minor rebound of the single throw.

Fair (a) Some stick-slip during run down. (b) Run-down force is somewhat high and minor damage to the sleeve fiber is noted. (c) Minor rebound of the single throw can occur.

Difficult/Poor (a) High stick-slip in run down. (b) High damage or even breaking of the strand occurs. (c) High rebound of the single throw occurs.

The suture strands coated only with the glycolide/TMC copolymer of Formulation 1 were rated between Excellent and Good. The suture strands coated with the mixture of Verv TM and the glycolide/TMC copolymer of Formulation 2 were rated Fair. The suture strands coated with the mixture of Verv TM and the glycolide/TMC copolymer of Formulation 3 were rated Excellent.

We claim:

1. A suture coating comprising a random copolymer having about 25 to 75 weight percent of glycolic acid ester linkages and the remaining linkages comprising trimethylene carbonate, said copolymer having a glass transition temperature at or below ambient temperature.

2. A coating of claim 1 wherein the glycolic acid ester linkages comprise from about 45 to 65 percent.

3. A coating of claim 2 wherein the glycolic acid ester linkages are about 50 percent.

4. A coating of claim 2 wherein the inherent viscosity as measured on a 0.5% solution in hexafluoroacetone sesquihydrate is between 0.5 and 3 dl/g.

5. A suture coating for a bioabsorbable suture comprising a bioabsorbable random copolymer having up to about 75 weight percent of glycolic acid ester linkages and the remaining linkages comprising trimethylene carbonate, said copolymer having a glass transition temperature at or below ambient temperature.

6. A coating of claim 5 wherein the glycolic acid ester and trimethylene carbonate linkages are each about 50 percent.

7. A coating of claim 6 wherein the inherent viscosity is from 0.5 to 3 dl/g.

8. A coating of claim 7 wherein the in vivo absorption time is less than one year.

9. A suture coating for a synthetic bioabsorbable suture comprising a bioabsorbable random copolymer having up to about 75 weight percent of glycolic acid ester linkages and the remaining linkages comprising trimethylene carbonate, said copolymer having an in vivo absorption time in living animal tissue of less than one year, an inherent viscosity of 0.5 to 3.0 dl/g, and a glass transition temperature of less than about 25° C. in combination with a lubricant additive of a stearoyl lactylate having the formula:

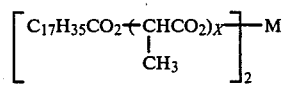

wherein X is at least two and M is an alkaline-earth metal.

10. A coating of claim 9 wherein the glycolic acid ester linkages are about 50 percent.

11. A coating of claim 10 wherein the glass transition temperature is 0° to 5° C.

* * * * *